(12) United States Patent
Breidenthal et al.

(10) Patent No.: US 7,621,868 B2
(45) Date of Patent: Nov. 24, 2009

(54) CONVERGENCE OPTICS FOR STEREOSCOPIC IMAGING SYSTEMS

(75) Inventors: Robert S. Breidenthal, Bolton, MA (US); Richard G. Cyr, New Ipswich, NH (US); Christopher David, Fitchburg, MA (US); Joseph N. Forkey, Princeton, MA (US); Richard E. Forkey, Westminster, MA (US); Robert N. Ross, Gardner, MA (US); Brian E. Volk, Jefferson, MA (US)

(73) Assignee: Precision Optics Corporation, Gardner, MA (US)

( * ) Notice: Subject to any disclaimer, the term of this patent is extended or adjusted under 35 U.S.C. 154(b) by 869 days.

(21) Appl. No.: 10/905,653

(22) Filed: Jan. 14, 2005

(65) Prior Publication Data

US 2005/0154256 A1 Jul. 14, 2005

(51) Int. Cl.
*A61B 1/06* (2006.01)
(52) U.S. Cl. ...................................... 600/166
(58) Field of Classification Search ............... 348/42, 348/45, 54; 600/111, 166; 359/372–378, 359/462, 471–473
See application file for complete search history.

(56) References Cited

U.S. PATENT DOCUMENTS

| | | | |
|---|---|---|---|
| 3,418,044 A * | 12/1968 | Sheldon | 353/7 |
| 4,364,629 A | 12/1982 | Lang et al. | |
| 4,723,842 A * | 2/1988 | Twisselmann et al. | 359/372 |
| 5,222,482 A * | 6/1993 | Clark | 600/111 |
| 5,341,240 A | 8/1994 | Broome | |
| 5,355,253 A * | 10/1994 | Nanjo et al. | 359/473 |
| 5,527,263 A * | 6/1996 | Zobel et al. | 600/166 |
| 5,589,956 A | 12/1996 | Morishima et al. | 359/15 |
| 5,702,350 A * | 12/1997 | Vry et al. | 600/166 |
| 5,825,539 A | 10/1998 | Hoshi | 359/462 |
| 6,104,426 A * | 8/2000 | Street | 348/45 |
| 6,139,490 A | 10/2000 | Breidenthal et al. | 600/111 |
| 6,309,348 B1 | 10/2001 | Schmidt et al. | |
| 6,324,001 B2 | 11/2001 | Tabata | 359/462 |
| 6,517,479 B1 * | 2/2003 | Sekiya et al. | 600/166 |
| 6,882,473 B2 * | 4/2005 | Geier et al. | 359/464 |
| 2003/0044060 A1 | 3/2003 | Martins | 382/154 |
| 2003/0083551 A1 | 5/2003 | Takahashi | |

* cited by examiner

*Primary Examiner*—John P Leubecker
*Assistant Examiner*—Philip R Smith
(74) *Attorney, Agent, or Firm*—George A. Herbster

(57) ABSTRACT

A convergence prism assembly with a housing and a prism structure having a plurality of prisms mounted in a unitary assembly.

8 Claims, 3 Drawing Sheets

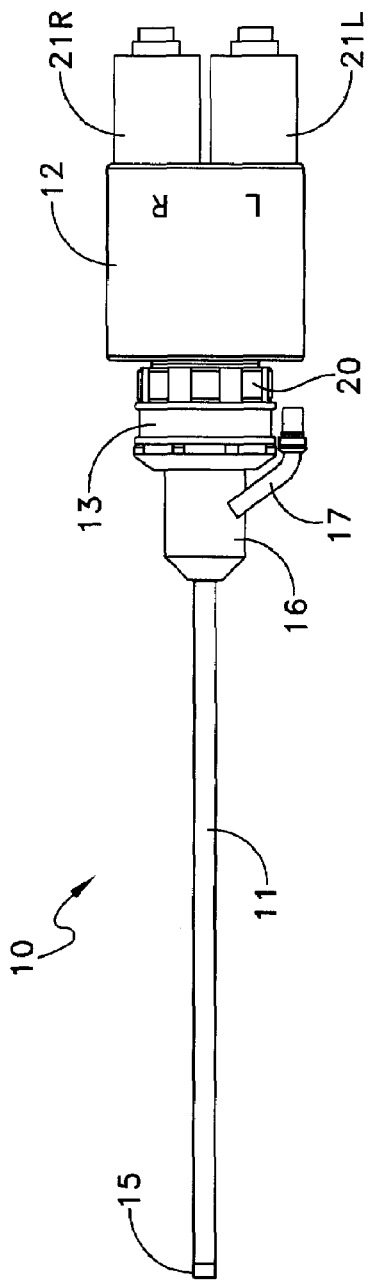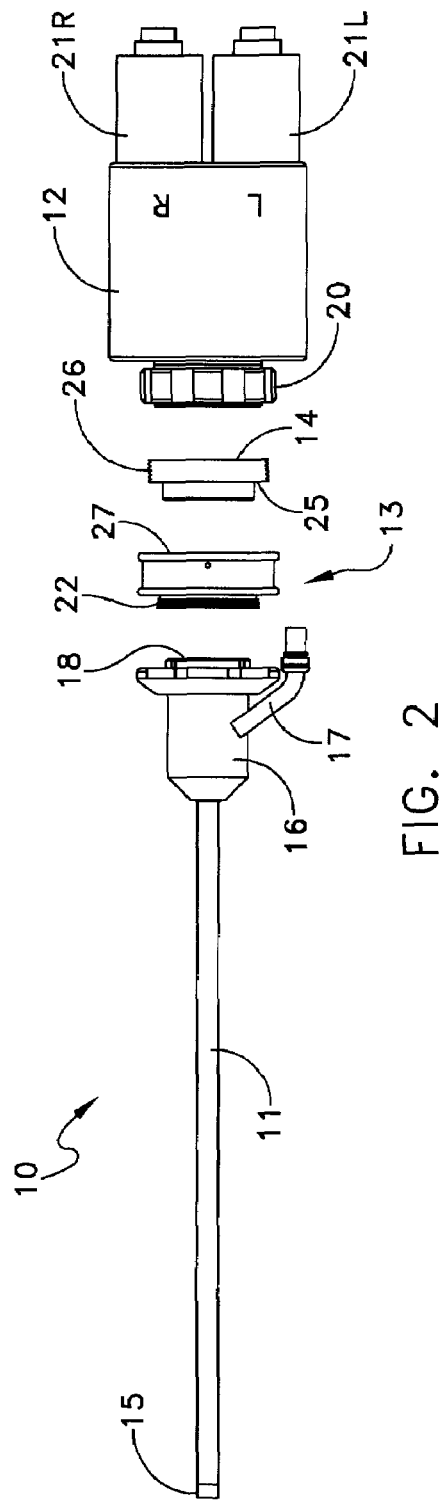

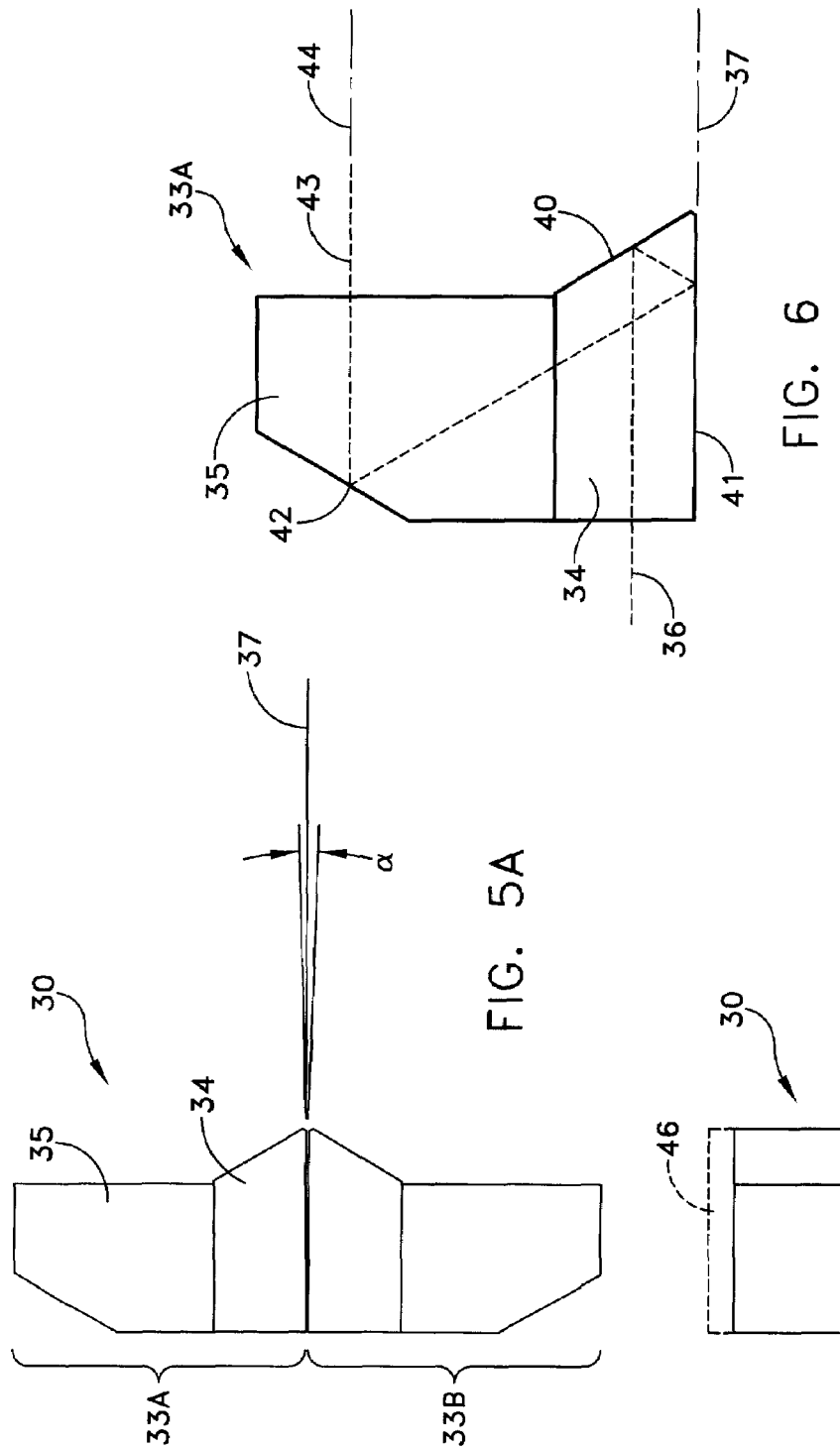

CONVERGENCE OPTICS FOR STEREOSCOPIC IMAGING SYSTEMS

FIELD OF THE INVENTION

This invention generally relates to convergence optics used in stereoscopic imaging and viewing systems and more particularly to convergence optics useful with endoscopes that facilitate three-dimensional, or stereoscopic, viewing.

DESCRIPTION OF RELATED ART

Endoscopes are examples of imaging systems that have attained great acceptance within the medical community in connection with a number of procedures. This acceptance exists because an endoscope provides a mechanism for performing procedures with minimal patient trauma while enabling a physician to view directly the internal anatomy of a patient. Over the years a number of endoscopes have been developed and have been categorized according to specific applications. Many have specific names including arthroscopes, cystoscopes, proctoscopes, laparoscopes and laryngoscopes. Industrial endoscopes are often called borescopes.

In whatever specific form, endoscopes and other similar imaging systems generally comprise an objective lens system at a distal end that forms an image of an object. With medical endoscopes the object generally is within a patient in some environmental media such as air, water, a saline solution or the like. Industrial endoscopes image objects that may be located in a remote enclosed volume. An ocular device at the proximal end presents the image for viewing visually, electronically or otherwise externally of the patient or enclosed volume. An eyepiece is an example of an ocular device that provides direct visual viewing. An image transfer system intermediate the objective lens system and ocular device transfers the image produced by the objective lens system to the ocular device.

Significant efforts have been undertaken to improve the optical designs of these endoscopes with attention at various times directed to individual constituent optical systems. For example, U.S. Pat. No. 6,139,490 (2000) discloses a stereoscopic endoscope with virtual reality viewing. Specifically, this patent discloses a stereoscopic endoscope system for producing images that can be perceived in three dimensions. The endoscope system includes a sheath carrying a light source and two independent endoscopes. Collimated light from the proximal end of each endoscope is directed along folded optical paths to independent video cameras. The images generated by the video cameras energize monitors in a virtual reality display device that can be positioned proximate an observer's eyes. Adjustable mirrors and other devices constitute convergence optics that facilitate the separation of the images for maximum effect.

Stereoscopic endoscopes and like imaging systems are generally self-contained. That is, each endoscope contains all of the optics necessary to project two images to a two-channel viewing device, such as a stereo video camera. Each of these endoscopes can be defined by different parameters including a working distance that establishes the field of view and magnification of the viewed image. The working distance is the expected distance between the distal end of the endoscope and the object to be viewed. Another parameter for stereoscopic imaging systems is convergence distance. The convergence distance is the distance between a reference point on an object and the entrance pupil when the two stereo images of the reference point appear to be coincident. As the use of these stereoscopic systems has increased, physicians have requested systems optimized for different working distances so that they can view an object with different magnifications without deterioration of the stereoscopic image.

Some prior art endoscopes, including stereoscopic endoscopes, are fixed-focus devices with self-contained optics and a characteristic depth of field. Consequently, it is possible to move the distal end of the endoscope over a limited range of working distances while maintaining adequate focus. Other endoscopes can be focused, so the endoscope can be moved over a wide range of working distances. However, even within the limited range of motion allowed by the depth of field in a fixed-focus endoscope, changing the working distance from the nominal or design working distance can cause the three-dimensional effect to deteriorate.

Specifically, the separation of the images at a viewing system changes as the working distance changes if the convergence distance is held constant. It is the convergence distance that determines the separation of the two images from the endoscope at the viewing system. Thus, it became necessary to design different endoscopes for different working distances in order to match the convergence distance to the working distance to provide both adequate focus and reasonable three-dimensional images. As a result, physicians requiring stereoscopic endoscopes with different working distances have been faced with the purchase of multiple, expensive stereoscopic endoscopes to maintain appropriate image separation.

In these endoscopes, the optics that convey the two output images to the viewing site comprise discrete, independently mechanically supported assemblies of optical elements. Moreover, these assemblies generally are present in non-collimated image space. They must be aligned relative to each other with greater precision and greater stability than is required for optical elements utilized in monoendoscopes. The requirement for greater precision and stability must be met to sustain the quality of the generated stereoscopic image.

Within the mechanical confines of acceptable endoscope packaging, the number of such optical elements can reduce the volume available for support structures and required geometries which are not amenable to standard sealing techniques required for autoclaving. Oftentimes, these optical elements have different sizes. These endoscopes are subject to damage during rough handling as, for example, when an endoscope is dropped accidentally. Autoclaving for sterilization introduces mechanical stress due to differential thermal expansion of differently sized components. Either effect can misalign the optical elements that define the convergence distance. Any such misalignment can change the convergence distance, overall optical characteristics of the endoscope or other stereoscopic imaging system and particularly the quality of the viewed three-dimensional image.

What is needed is an apparatus that enables a single stereoscopic imaging system, such as an endoscope, to be adapted for different working distances, that enables such an imaging system to withstand rough handling and the stresses of repetitive autoclaving and that facilitates the precise alignment of the optical elements that define the convergence distance.

SUMMARY

Therefore, it is an object of this invention to provide a stereoscopic imaging system with a means for providing different convergence distances by means of interchangeable convergence optics.

Another object of this invention is to provide stereo convergence optics with optical elements that are more easily aligned, and that have an increased stability with respect to environmental loads.

Still another object of this invention is to provide a stereoscopic viewing system using an endoscope as an imaging system with couplers that are characterized by different convergence distances.

Yet another object of this invention is to provide convergence optics for a stereoscopic endoscope viewing system that can withstand various environmental loads, such as mechanical and thermal shock.

Still yet another object of this invention is to provide convergence optics for a stereoscopic endoscope that minimizes the impact of repeated autoclaving of the endoscope.

In accordance with one aspect of this invention a convergence coupler connects between a stereoscopic imaging system and a stereoscopic viewing system. A housing is adapted for detachable connection intermediate the imaging and viewing systems. Convergence optics in the housing transfers a light ray received along an incoming axis from the imaging system to the stereoscopic viewing system along a different output axis to provide optimal convergence for stereoscopic viewing.

In accordance with another aspect of this invention an optical stereoscopic system includes an optical imaging system and viewing system. The optical imaging systems provides first and second separate images of an object and light transferred through first and second optical channels. The viewing system presents the images for stereoscopic viewing. First and second optical assemblies, including only prisms, control the transfer of light from the first and second optical channels to optimize stereoscopic viewing.

In accordance with still another aspect of this invention, an optical stereoscopic system includes an optical imaging system and a viewing system. The optical imaging system provides first and second separate images of an object in collimated light transferred from the first and second optical channels. An optical convergence assembly includes first and second optical assemblies that redirect light rays from a single object point and transferred through the first and second optical channels along first and second output axes respectively. The first and second optical assemblies are positioned whereby the first and second output axes have an included angle that optimizes the separation of images at the viewing system.

In yet another aspect of this invention, an optical convergence coupler is adapted for connection between a stereoscopic endoscope that produces separate images of an object at two channels in a stereoscopic viewing system. The optical convergence coupler includes a housing with a cavity adapted for detachable connection intermediate the endoscope and viewing system. Convergence optics in the housing cavity redirects light from each endoscope channel to the stereoscopic viewing system thereby to establish image separation at the viewing system that provides an optimal stereoscopic image of the object for viewing.

In accordance with still yet another aspect of this invention, an optical system for viewing an object stereoscopically comprises a stereoscopic endoscope and a stereoscopic viewing system. The stereoscopic endoscope transmits images of an object along each of two channels wherein the object is located at a working distance from a distal end of the endoscope. The stereoscopic viewing system displays a stereoscopic image in response to the incoming images. Convergence optics intermediate the endoscope and viewing system establish an optimal convergence distance for images from the stereoscopic image system for a given working distance. More specifically, a first optical assembly transfers a light ray from an object point received from the first channel along a first input axis to the viewing system along a first output axis. A second optical assembly transfers a light ray from the same object point received from the second channel along the second input axis to the viewing system along a second output axis. The first and second output axes are oriented to be complementary and define an included angle therebetween that optimizes the image separation at the viewing system for the working distance.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 1 is a plan view of an endoscope assembly that incorporates this invention;

FIG. 2 is an exploded view of the endoscope assembly that is shown in FIG. 1;

FIGS. 5A and 5B are top and side plan views of the prism assembly included in the convergence assembly of FIGS. 3 and 4; and FIG. 6 is an enlarged view of a portion of the prism assembly shown in FIG. 5.

DESCRIPTION OF ILLUSTRATIVE EMBODIMENTS

Figure 3:
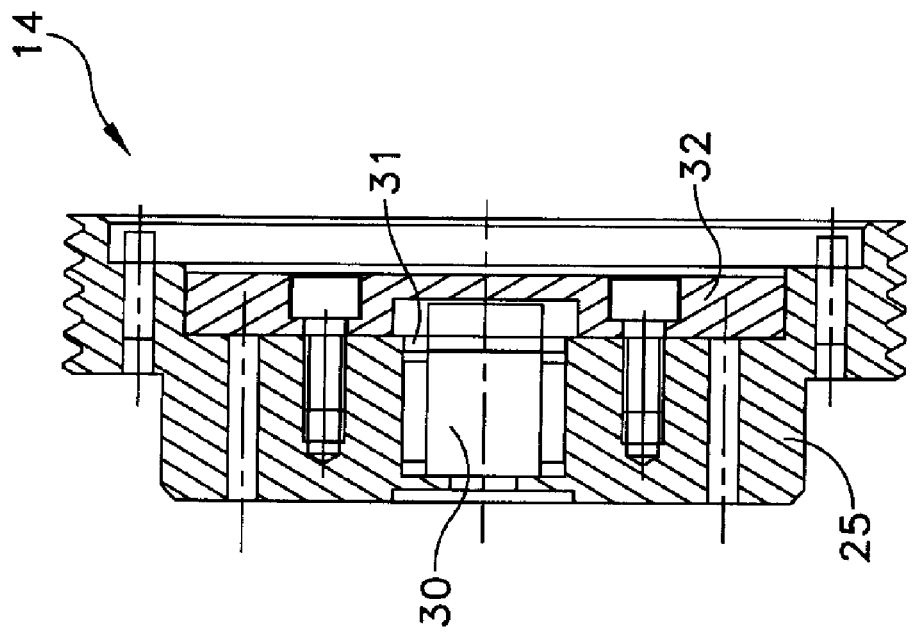
FIG. 3 is a cross-section through a prism-based convergence assembly in the plane of FIG. 1.

As shown in FIGS. 1 and 2, an endoscope assembly 10, as an example of an optical stereoscopic system incorporating this invention, includes an endoscope 11 as an imaging system, a camera assembly 12 representing a viewing system, an adapter 13 and a convergence coupler 14. The endoscope 11 carries an objective lens at a distal end 15, relay lenses and an ocular device at the proximal end 16. A light pipe connection 17 provides a means for connecting to a light source to provide illumination at the distal end 15 to illuminate an object. The proximal end 16 also includes an externally threaded coupling 18.

The camera assembly 12 included in a viewing system can take many forms. In this specific embodiment, the camera assembly 12 includes a front end coupling 20 and left and right cameras 21L and 21R. Internal camera optical elements accept collimated light from the ocular device 13 and flip and focus images onto the light sensitive detectors to produce electronic signals that the viewing system converts to a viewable stereoscopic image, all as known in the art.

The adapter 13 includes an externally threaded collar 22 facing to the left in FIGS. 1 and 2. This collar 22 threads onto the coupling 18 thereby to attach the adapter 13 to the endoscope 11 through a detachable connection. Typically the adapter 13 includes a surface for attaching a sterile drape thereby to define a sterile field for the endoscope and a non-sterile field for the camera assembly 12.

In this embodiment the convergence coupler 14 has a housing 25 with an externally threaded portion 26 that threads into an internally threaded cavity 27 in the adapter 13, facing to the right in FIG. 2. The externally threaded portion 26 of the housing 25 is also mated into a coupling 20 on the camera 12 by rotating the coupling 20 to form another detachable connection. Thus, when the endoscope 11, adapter 13, convergence coupler 14 and camera 12 are assembled, they form the endoscope based optical system assembly 10 that is a rigid structure and that produces a stereoscopic display of an object.

As will become apparent, it is a straightforward matter to construct convergence couplers 14 embodying this invention with different characteristics to match different working distances. Then it is a simple procedure for a physician to exchange convergence couplers. Thus, this invention enables a physician to purchase a single stereoscopic endoscope and a set of convergence couplers 14 and to install a convergence coupler that matches the working distance the physician expects to encounter during a procedure.

Moreover, in accordance with this invention, locating optical elements in the convergence coupler 14 and externally of the endoscope 11 simplifies the construction of the endoscope 11. Specifically, removing the convergence optics from the endoscope 11 simplifies the construction of the endoscope so the endoscope is more tolerant of repeated autoclaving. Also, the convergence coupler 14 can be located outside a sterile field, so the convergence coupler typically will not need to be autoclaved. However, the coupler 14 can be constructed to be autoclaved should that requirement exist.

Now referring to optical characteristics, the endoscope 11 is formed as a stereo endoscope with two separate imaging systems or channels. This means that the endoscope 11 has individual separated entrance pupils with a transverse separation "b" from center to center of the individual channels. The images produced by the two channels are in register when imaging an object field located on axis at a convergence distance "h" distally from the entrance pupil locations. As known, the entrance pupils will be approximately located at the distal end 15.

The ratio of "b" to "h" is an important characteristic because this ratio determines whether an endoscope provides appropriate stereo separation for a given working distance. In order to maintain a focused image at the sensor, defined as the focal plane of the camera assembly 12 for example, many stereoscopic endoscopes provide a range of working distances through the use of focusing mechanisms. However, it is necessary to provide an optimal convergence distance that typically corresponds to the working distance if the three-dimensional effect is to be maintained in a relatively consistent state when such refocusing occurs. That is, it is necessary to use a mechanism for adjusting the convergence distance "h" to match the working distance established by the focus.

The convergence coupler 14 constitutes a means for providing a predetermined convergence distance. The convergence coupler 14 conveys the images from the endoscope channels to the viewing device and establishes the convergence distance for the endoscope to match with the appropriate working distance. As a result, it is merely necessary to exchange convergence assemblies to effect a change in the convergence distance and optimize the stereo images for a maximum three-dimensional effect.

More specifically, the convergence coupler 14 sets the convergence distance by differentially redirecting the collimated light from the two channels of the endoscope 11 before the collimated light enters the camera assembly 12. Setting the convergence point by redirecting the image forming light in a location where it is collimated, as opposed to where it is converging or diverging, simplifies design and alignment of optical elements.

Figure 4:
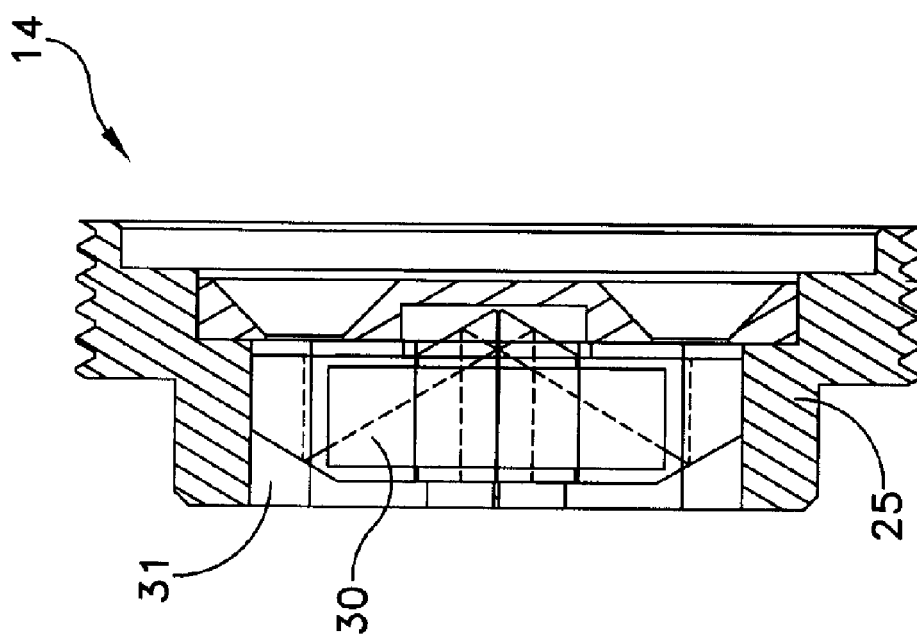
FIG. 4 is another cross-section through the prism-based convergence assembly shown in FIG. 1 that is transverse to the cross-section view of FIG. 3.

FIGS. 3 and 4 depict one embodiment of a convergence coupler 14 that includes the housing 25 with the externally threaded portion 26. The housing 25 receives a convergence prism assembly 30 in a rectangular cavity 31. A retaining cover 32 locks the convergence prism assembly 30 in the housing 25. The details of this structure will depend primarily upon the specific implementation of the convergence prism assembly 30. It is sufficient to say that the housing 25 and retaining cover 32 should be constructed with openings so that they do not interfere with any of the optical paths.

Now referring to FIGS. 5A and 5B, the specifically disclosed convergence prism assembly 30 comprises two optical assemblies 33A and 33B. They are identical counterfacing assemblies, so only the optical assembly 33A need be described. As shown in FIGS. 5A and 6, the optical assembly 33A includes only prisms, in this embodiment two contiguous optical prisms 34 and 35. More specifically, in this embodiment, the first prism 34 is four sided; the second prism 35 is five sided. An incoming light ray from a single object point undergoes two reflections in the prism 34 and one reflection in the prism 35.

Referring to FIG. 6 an incoming light ray 36 from a single object point transferred through one channel of the endoscope lies on an input axis parallel to an axis 37. The light ray 36 reflects from a mirrored prism face 40 and a mirrored prism face 41 of the first prism 34 and from a mirrored prism face 42 of the second prism 35 to exit the assembly 33A as an output ray 43 along an output axis 44. The input and output axes for a light ray are parallel. As will also be apparent, other incoming light rays from an image can enter the prism 33A at any angle and collectively the light rays will be transmitted along corresponding axes at the output.

The prism face 41 also defines a reference. If the assembly 33A is rotated about an axis perpendicular to the plane of FIG. 6, reference face 41 no longer lies along axis 37, and the axis 44 defined by light ray 43 no longer is parallel to axis 37. These corresponding axes at the output will depend on the rotation of the assembly 33A about an axis perpendicular to the plane of FIG. 6. It will also be apparent that the optical assembly 33B upon rotation will produce a complementary output of the image from the other channel of the endoscope 11. The rotation typically will be equal in magnitude and opposite in direction.

In accordance with one embodiment of this invention, the process of manufacturing the convergence prism assembly 30 includes mounting each of the assemblies 33A and 33B in a jig or fixture that allows them to be rotated about axes, that would be perpendicular to the plane of FIG. 5A. They are rotated until the included angle between the counterfacing reference faces optimizes the separation of images at the viewing system.

In one manufacturing approach, glass plates are cemented to each side of the convergence prism assembly 30 once the appropriate included angle has been set. FIG. 5B shows two such plates 46 and 47 in phantom. This construction and manufacturing process enables the physical construction of a beam deviating prism, such as the convergence prism assembly 30, with a very high accuracy. It also allows for the alignment of reflecting surfaces, such as reflecting surfaces 40, 41 and 42, to be achieved using known techniques for prism fabrication, which are easier and more precise than alignment of equivalent mirrors used in conventional stereo endoscopes. Also, in its final form with the plates 46 and 47, the convergence prism assembly 30 is essentially monolithic and therefore is highly stable under a wide range of environmental loads.

Therefore, the convergence coupler 14 is readily attached and detached from an endoscope assembly. A variety of convergence couplers 14 can be inventoried for different working distances without the need for a different endoscope for each working distance. This will reduce the acquisition costs for endoscope systems for a wide variety of applications. The relocation of convergence optical elements to a separate convergence coupler 14, instead of within the endoscope 11, allows the endoscope 11 to be more robust for autoclaving and allows for the use of traditional sealing techniques for autoclavable instruments. There are benefits realized when the beam deviation required to set the convergence distance is accomplished by the convergence coupler 14 in collimated space. As one, the viewed images are less sensitive to many imperfections that may exist in the optical elements. Also, there is a greater flexibility in design because there typically is less sensitivity to aberrations caused by glass path variations in prisms.

This invention has been disclosed in terms of certain embodiments. For example, the specific embodiment of this invention discloses the convergence coupler 14 as a separate device. In some applications the convergence coupler 14 may be permanently attached to a camera assembly, such as the camera assembly 12. This would still enable the advantage of allowing a single endoscope to be used for different working distances by providing the physician with different camera units. Also, the convergence coupler 14 is located in collimated space in the specifically disclosed embodiment. The invention is also readily adapted for locating a coupler 14 in non-collimated space. The specific embodiment discloses an optical assembly using a four-sided and a five-sided prism. Other equivalent prisms could be substituted or modified to perform the same function. It will be apparent that the foregoing and many other modifications can be made to the disclosed apparatus without departing from the invention. Therefore, it is the intent of the appended claims to cover all such variations and modifications as come within the true spirit and scope of this invention.

What is claimed is:

1. An optical system for viewing an object stereoscopically comprising:
   A) a stereoscopic endoscope for transmitting images of the object along each of two channels wherein the object is located at a working distance from a distal end of said endoscope,
   B) a stereoscopic viewing system that displays a stereoscopic image in response to incoming images, and
   C) one of a plurality of convergence couplers intermediate said endoscope and said viewing system for differentially redirecting the light collected from the object to the stereoscopic viewing system whereby each convergence coupler provides an optimal convergence distance for stereoscopic viewing for a different working distance whereby an exchange of said convergence couplers modifies the image convergence to accommodate different working distances, each said convergence coupler including:
   i) a first optical assembly for transferring a first light ray from an object point received from the first channel along a first input axis to said viewing system along a first output axis,
   ii) a second optical assembly for transferring a second light ray from the same object point received along a second input axis from the second channel to said viewing system along a second output axis,
   iii) each of said first and second optical assemblies including first and second contiguous optical elements that redirect the first and second light rays correspondingly, and
   iv) means for orienting said first and second optical assemblies relative to a reference plane whereby said first and second output axes are complementary and define an angle therebetween that optimizes the image separation at the viewing system for the corresponding working distance.

2. An optical system as recited in claim 1 including means for releasably connecting said convergence coupler intermediate said endoscope and said viewing system thereby to enable said convergence couplers to be exchanged to compensate different working distances.

3. An optical system as recited in claim 2 wherein said endoscope has an eyepiece wherein said convergence coupler includes a housing for said first and second optical assemblies and said orienting means and wherein said releasable connecting means includes a first releasable coupling for connection to said eyepiece and a second releasable coupling for connection to said viewing system.

4. An optical system as recited in claim 2 wherein each of said first and second optical assemblies includes a first prism for directing light received along a respective input axis to a contiguous second prism for directing light along a respective output axis, said first prism having a reference face from which light received along the input axis reflects and wherein said orienting means engages said prisms to establish an included angle between said reference faces.

5. An optical system as recited in claim 4 wherein said second prism in each of said first and second optical assemblies is a five-sided prism.

6. An optical system as recited in claim 5 wherein said first prism in each of said first and second optical assemblies is a four-sided prism.

7. An optical system as recited in claim 2 wherein each of said first and second optical assemblies includes prism means including three reflecting surfaces for redirecting light from an input axis to an output axis.

8. An optical system as recited in claim 7 wherein each of said prism means includes a first prism with two reflecting surfaces for receiving light from a corresponding input axis and a contiguous second prism with one reflecting surface for directing light received from said first prism along the output axis.

* * * * *